(12) United States Patent
Hoelzl et al.

(10) Patent No.: US 7,423,424 B2
(45) Date of Patent: Sep. 9, 2008

(54) METHOD AND APPARATUS FOR THE NON-DESTRUCTIVE AND CONTACTLESS DETECTION OF FAULTS IN A TEST PIECE WHICH IS MOVED RELATIVE TO A PROBE

(75) Inventors: Roland Hoelzl, Munich (DE); Michael Hermann, Villingen-Schwenningen (DE)

(73) Assignee: Prüftechnik Dieter Busch AG, Ismaning (DE)

( * ) Notice: Subject to any disclaimer, the term of this patent is extended or adjusted under 35 U.S.C. 154(b) by 300 days.

(21) Appl. No.: 10/595,899

(22) PCT Filed: Jul. 18, 2005

(86) PCT No.: PCT/DE2005/001263

§ 371 (c)(1),
(2), (4) Date: May 18, 2006

(87) PCT Pub. No.: WO2006/007826

PCT Pub. Date: Jan. 26, 2006

(65) Prior Publication Data

US 2007/0080681 A1    Apr. 12, 2007

(30) Foreign Application Priority Data

| Jul. 19, 2004 | (DE) | 10 2004 034 881 |
| Aug. 12, 2004 | (DE) | 10 2004 039 348 |
| Aug. 23, 2004 | (DE) | 10 2004 040 860 |
| Oct. 21, 2004 | (DE) | 10 2004 051 506 |
| Oct. 25, 2004 | (DE) | 10 2004 051 949 |

(51) Int. Cl.
  *G01N 27/82* (2006.01)
  *G01N 27/90* (2006.01)
(52) U.S. Cl. .................................... 324/240

(58) Field of Classification Search ............. 324/202, 324/222, 228–232, 239–243, 326–329, 67
See application file for complete search history.

(56) References Cited

U.S. PATENT DOCUMENTS 4,083,002 A * 4/1978 Allport .................. 324/227
4,445,088 A    4/1984 Schübel (Continued)

FOREIGN PATENT DOCUMENTS

WO    WO 95/16912 A1    6/1995

*Primary Examiner*—Reena Aurora
*Assistant Examiner*—Kenneth J Whittington
(74) *Attorney, Agent, or Firm*—David S. Safran

(57) ABSTRACT

Method for nondestructive and contact-free detection of faults in a test specimen which is moved relative to a probe that detects a periodic electrical signal having a carrier oscillation whose amplitude and/or phase is/are modulated by any fault in the test specimen. The probe signal is filtered and sampled by a triggerable A/D converter stage to obtain a demodulated digital measurement signal which is filtered using a digital frequency-selective adjustable second filter unit to obtain a useful signal which is evaluated to detect a fault in the test specimen. The A/D converter stage is triggered at a fraction of the frequency of the carrier oscillation selected as a function of the fault frequency obtained as the quotient of the relative speed between the test specimen and the probe and the effective width of the probe, and the frequency-selective second filter unit is adjusted as a function of the fault frequency.

34 Claims, 2 Drawing Sheets

U.S. PATENT DOCUMENTS

| | | | | |
|---|---|---|---|---|
| 4,651,091 A | * | 3/1987 | Chambers et al. | 324/204 |
| 5,175,498 A | | 12/1992 | Cueman et al. | |
| 5,424,640 A | | 6/1995 | Levy | |
| 5,570,017 A | * | 10/1996 | Blum | 324/232 |
| 6,566,871 B2 | * | 5/2003 | Holzl | 324/240 |

* cited by examiner

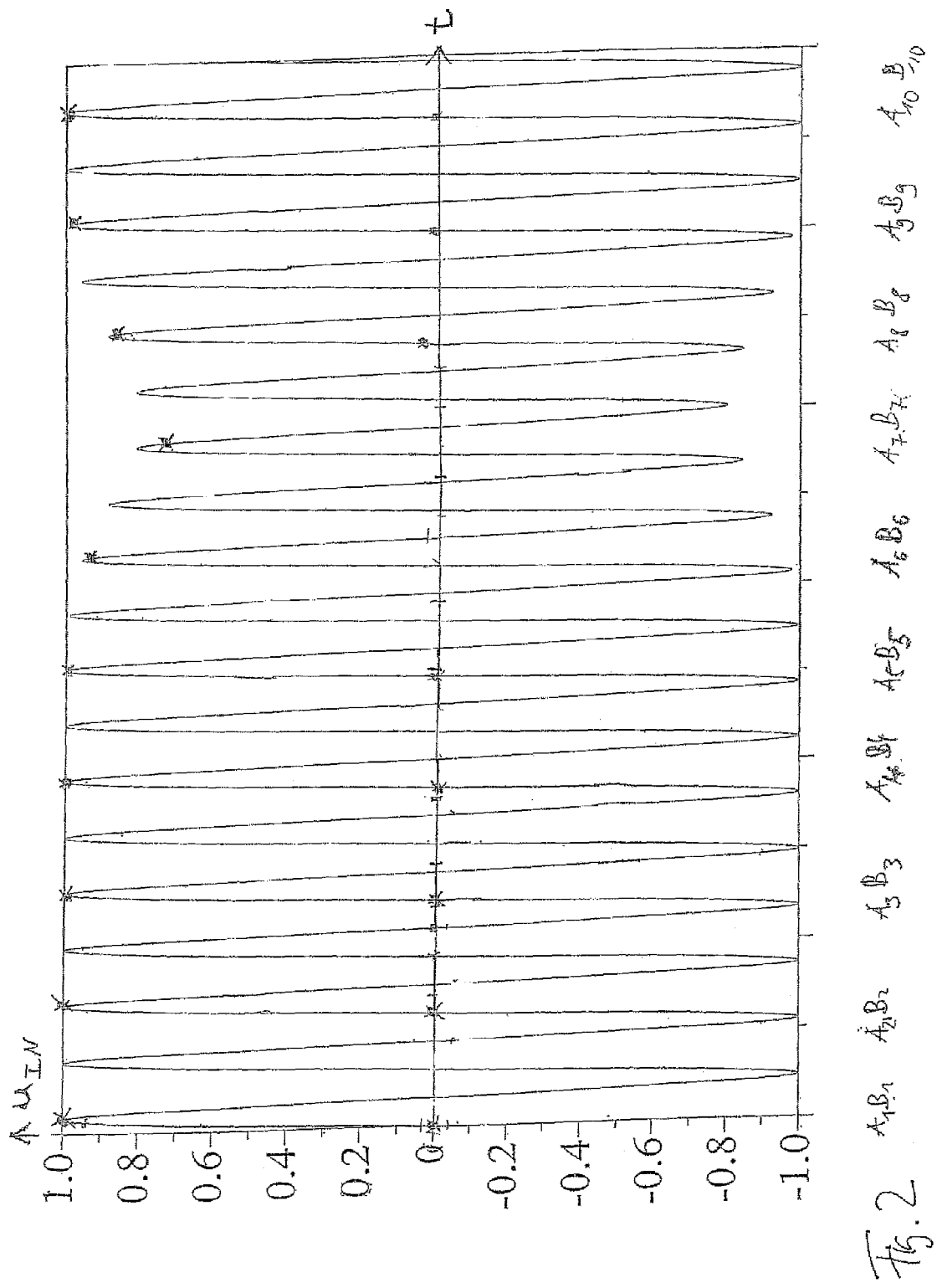

METHOD AND APPARATUS FOR THE NON-DESTRUCTIVE AND CONTACTLESS DETECTION OF FAULTS IN A TEST PIECE WHICH IS MOVED RELATIVE TO A PROBE

BACKGROUND OF THE INVENTION

1. Field of the Invention

The present invention relates to a method and an apparatus for the nondestructive and contact-free detection of faults, particularly by means of eddy currents, in a test specimen which is moved relative to a probe that is characterized by an effective width.

2. Description of Related Art

A conventional measurement method for the nondestructive and contact-free detection of faults in a test specimen, in particular a metal semifinished product, is to induce and measure eddy currents in the test specimen. In this case, periodic electromagnetic alternating fields are applied to the test specimen using a transmission coil which is energized sinusoidally. The eddy currents which are thereby induced in the test specimen, in turn, induce a periodic electrical signal in a coil arrangement which is used as a probe and can have an individual coil ("absolute coil") or two coils which are connected subtractively ("differential coil"), the electrical signal having a carrier oscillation corresponding to the transmitter carrier frequency, the amplitude and/or phase of which is/are modulated in a characteristic manner as a result of a fault in the test specimen if a fault reaches the sensitive region of the probe, i.e., the effective width of the probe. In order to scan the test specimen, the test specimen is usually moved linearly with respect to the probe, but arrangements having a rotating probe are also known. The signal detected by the probe is usually demodulated in an analog manner, for example, using synchronous demodulation, and is then evaluated in order to detect faults in the test specimen. In this case, the signal is usually digitized only for the evaluation and representation of the fault signal, that is to say after the coil signal has been demodulated.

Such eddy current measurement methods are relatively complicated and expensive on account of the outlay needed for the analog demodulation. It must also be taken into account that for different relative speeds between the test specimen and the probe, that is to say in the case of different output rates and test speeds, different sets of filters are usually required for the demodulated signal, thus entailing additional outlay in the case of a variable test specimen speed.

U.S. Pat. No. 5,175,498 describes an eddy current measurement method in which even the measurement signal which has been picked up by the coil probe is digitized using a triggerable A/D converter and is then filtered in digital form using Fourier transformation. Triggering of the A/D converter, i.e., the sampling rate, is controlled as a function of the forward feed speed (detected using an encoder) of the test specimen in order to avoid errors (which result from the test specimen being moved backward) when evaluating the signal.

U.S. Pat. No. 4,445,088 describes a stray magnetic flux measurement method in which a metal test specimen is moved relative to a probe, the measurement signal detected by the probe being digitized using a triggerable A/D converter after said signal has passed through a bandpass filter, and triggering of the converter, i.e., the sampling rate, being controlled by the forward feed speed (detected using a speed sensor) of the test specimen. In order to detect faults, the amplitude of the digitized signal is evaluated in order to determine whether it has exceeded a threshold value, the selection of the sampling rate as a function of the testing speed being used to achieve a prescribed measurement accuracy that is independent of the test specimen speed.

SUMMARY OF THE INVENTION

It is an object of the present invention to provide a particularly simple method for the nondestructive and contact-free detection of faults in a moving test specimen, in which method a probe is used to detect a periodic electrical signal whose amplitude and/or phase is/are modulated as a result of faults in the test specimen. The intention is also to provide an apparatus which is suitable for carrying out such a method.

According to the invention, this object is achieved by the A/D converter stage being triggered at an nth integer fraction of the frequency of the carrier oscillation, n being selected as a function of the fault frequency which is obtained as the quotient of the relative speed between the test specimen and the probe and the effective width of the probe, and the frequency-selective second filter unit being adjusted as a function of the fault frequency.

One fundamental aspect of the present invention is that the probe signal is sampled. i.e., digitized, at an integer fraction of the frequency of the carrier oscillation, i.e., the carrier oscillation is undersampled.

This eliminates the carrier oscillation from the measurement signal, as a result of which the otherwise customary demodulation of the measurement signal is dispensed with and it is thus possible to considerably simplify the method and to considerably reduce the outlay for demodulation, for example, analog synchronous demodulation, which is otherwise required, thus resulting in considerable cost savings and, if appropriate, also in savings in installation space.

Undersampling also makes it possible to use A/D converters which have a very high resolution and are usually relatively slow, i.e., their maximum sampling rate is relatively restricted.

In addition, undersampling results in the useful signal being obtained at a relatively slow data rate, thus in turn, facilitating representation of the useful signal, with the result that standard bus systems and possibly radio bus systems can be used, for example, which would not be possible at high data rates or would be possible only after data compression.

Undersampling also allows the measurement method to be carried out with a relatively low power consumption, in which case the transmitter could be switched off, even during intervals of time in which no sampling is being effected, if sampling is effected, for example, only during every tenth period of the carrier oscillation or even more rarely. This aspect is particularly important for portable devices during battery operation or if a cableless (i.e., wirelessly connected to the evaluation unit) probe is to be used.

Finally, reduced (in comparison with quasi-continuous sampling) susceptibility to nonperiodic interference signals may result during undersampling since such interference signals are not perceived at all in the useful signal provided that they do not occur in the respective sampling period, whereas all of the interference signals are reflected in the useful signal in the case of quasi-continuous sampling.

In accordance with another fundamental aspect of the invention, the sampling rate, i.e., the degree of undersampling, is selected as a function of the so-called fault frequency, that is to say the quotient of the relative speed between the test specimen and the probe and the effective width of the probe.

Since the duration of the useful signal caused by a fault, and thus, the fault frequency, essentially depend only on the extent of the sensitive region of the probe, i.e., the effective width, and on the relative speed between the test specimen and the probe, it can be ensured in this manner, on the one hand, that the accuracy with which the useful signal is represented does not depend on the speed of the test specimen (it can be ensured, by appropriately selecting the sampling rate, that approximately the same number of sampling points always occur in each fault signal) and it can be ensured, on the other hand, that the fault signal of a particular fault essentially looks the same irrespective of the speed of the test specimen, thus greatly simplifying detection of the fault.

Another advantage of undersampling that is matched to the speed resides in the fact that, in this manner, the digital filter unit which is used to filter the digital measurement signal provided by the A/D converter stage in order to obtain an interference-free useful signal can be adjusted in a very simple manner as a function of the fault frequency, namely by clocking the digital filter at the sampling rate (in the case of a digital filter, the cut-off frequency depends directly on the clock rate). This makes it possible to use one single set of filters whose cut-off frequencies are automatically matched to the bandwidth (which is dependent on the test specimen speed) of the fault signal by appropriately selecting the sampling rate, i.e., the clock rate.

The so-called fault frequency usually corresponds to the maximum of the fault spectrum, i.e., the frequency with the highest intensity. The fault bandwidth is the frequency range around the fault frequency in which information that is still decisive for detecting faults or representing faults can be found. The effective width of the probe depends, on the one hand, on the geometric configuration of the probe but also on the boundary conditions for use of the probe, for example, the distance between the probe and the test specimen (filling factor), the frequency of the carrier oscillation, the material of the test specimen etc. Physically, the effective width corresponds to the length which corresponds to the reciprocal of the fault frequency and is obtained from the test specimen speed divided by twice the fault frequency. The effective width thus specifies the length over which a particular (fault) location in the test specimen can influence the measurement signal picked up by the probe.

The invention preferably uses the measurement of eddy currents in the test specimen, that is to say the transmitter is a coil to which a radiofrequency AC voltage, preferably in the frequency range from 1 kHz to 5 MHz, is applied in order to induce eddy currents in the test specimen, the probe being a coil arrangement in which the eddy currents induce the periodic signal. In this case, the probe is preferably in the form of a differential coil.

Alternatively, however the invention may also be based on a so-called EMAT (Electromagnetic Acoustic Transducer) method, the transmitter using electromagnetic excitation to generate sound waves in the test specimen, and the probe detecting sound waves in the test specimen and converting them into the periodic electrical signal.

In another variant, the invention may use microwave measurement, the transmitter radiating microwaves into the test specimen, and the probe converting microwaves into the periodic electrical signal.

The relative movement between the test specimen and the probe preferably results from the test specimen being moved linearly with respect to the probe. In principle, however, the relative movement between the test specimen and the probe may also result from the probe rotating with respect to the test specimen.

The AC voltage for the transmitter may be generated from a binary signal by means of curve shaping, the trigger signal for the A/D converter stage preferably being generated by the frequency of the binary signal that is used to generate the transmitter AC voltage being divided by an integer. The integer by which the frequency of the carrier oscillation is divided in order to trigger the A/D converter stage is preferably selected to be inversely proportional to the fault frequency so that the sampling rate selected may be selected to be at least approximately proportional to the fault frequency. This integer is preferably selected in such a manner that at least 5, preferably at least 20, but at most 100, preferably at most 50, sampling operations are effected by the A/D converter stage in a fault interval, i.e., an interval of time which corresponds to the inverse of the fault frequency.

As already mentioned, the frequency-selective second filter unit may be automatically adjusted as a function of the fault frequency by the second filter unit being clocked at the sampling rate for each A/D converter stage since, in the case of a digital filter, the cut-off frequency is directly proportional to the clock frequency. The second filter unit expediently has a low-pass filter in order to remove components outside the fault bandwidth and a high-pass filter in order to remove DC components of the digital signal. The cut-off frequency of the low-pass filter is expediently higher than the fault frequency, preferably higher than twice the fault frequency, while the cut-off frequency of the high-pass filter is less than the fault frequency, preferably less than a quarter of the fault frequency. Since the preferred cut-off frequencies of the second filter unit depend directly on the fault frequency, it is possible, by virtue of the sampling rate of the signal likewise being selected as a function of the fault frequency and the second filter unit being clocked at this sampling rate, to automatically optimally match the cut-off frequencies of the filter unit to the fault frequency, i.e., the test specimen speed and the effective width of the probe, in a particularly simple manner. In principle, the cut-off frequencies may be closer to the fault frequency than in conventional methods since, as a result of the filters being accurately tracked with respect to the fault frequency, i.e., the test specimen speed, in particular, the risk of the filters cutting off fault information is reduced.

The frequency of the carrier oscillation is preferably selected in such a manner that it is at least ten times, better still at least twenty times, the fault frequency since the ability to reproduce a fault (i.e., the ability to reproduce a fault signal that is typical of a particular fault) may otherwise be impaired, which would make it more difficult to detect faults.

Although solutions are also possible, in principle, in which only one individual value is detected for each full cycle sampled, in which case it would then be necessary to determine the phase angle indirectly, two values with a fixed phase offset are preferably obtained for each full cycle sampled, this preferably being carried out using two A/D converters, i.e., the converter stage has two A/D converters which are connected in parallel and are triggered at the same frequency in such a way that they sample in a manner offset by a fixed phase difference, the phase difference preferably being 90° or an integer multiple of 360° plus 90° (however, the phase difference need not necessarily be exactly 90° but rather could be between 85 and 95°, for example). Such phase-offset sampling can be used to ensure that, despite the undersampling, the maximum amount of signal information is obtained, and the digital measurement signal is obtained in the form of a two-component signal, i.e., with phase and amplitude information, thus improving the detection of faults. In this case, it is expedient for the two components of the digital measurement signal provided by the A/D converter stage equipped with two A/D converters to be filtered separately using the second filter unit in order to obtain the useful signal in the form of a two-component signal, the two components then being able to be taken into account when evaluating the useful signal.

In order to carry out such phase-offset sampling, it is not necessarily required to use precisely two A/D converters. Instead of this, it would also be possible to use only a single A/D converter which is sufficiently fast and carries out the two sampling operations, i.e., that at 0° and that at 90°, these two sample values then being processed further separately, as when using two A/D converters, in order to achieve two-component signal evaluation. It would be possible to use very slow A/D converters if, for example, use is made of 4, 8 or 16, etc. A/D converters which do not become active upon each trigger pulse that is applied to the A/D converter stage but rather only become active upon every 2nd, 4th or 8th etc. trigger pulse, i.e., the sampling work for each of the two phase angles is respectively appropriately divided, in terms of time, between a plurality of A/D converters.

The A/D converter stage preferably has a resolution of at least 16 bits, use preferably being made of flash converters or SAR converters.

The application, i.e., the radiation, of the electromagnetic alternating fields to the test specimen using the transmitter may, in principle, be interrupted at least for part of each interval between two successive trigger signals for the A/D converter stage since signals are not detected, i.e., sampled, anyway in this time (depending on the specific situation, these sampling pauses may, under certain circumstances, extend over a large number of periods of the carrier oscillation). This makes it possible, particularly in the case of portable measuring devices, to considerably save on power consumption, thus making it possible, for example, to considerably reduce the dimensions and weight of the power supply elements. In a similar manner, on the signal detection side, the electronics, i.e., the signal processing processor, in particular, may also be shut down in the interval between two sampling operations in order to save power.

The first filter unit preferably has a low-pass filter which acts as an aliasing filter as regards the sampling by the A/D converter stage, a high-pass filter also preferably being provided in order to remove low-frequency interference signals. The first filter unit is usually in the form of an analog filter. A controllable amplifier is preferably also provided downstream of the first filter unit in order to change the filter signal to the amplitude that is optimally suited to the A/D converter stage.

The speed of the test specimen is preferably determined by means of measurement, for example, using an encoder. If it is not absolutely necessary to measure the testing speed because, for example, it is known anyway with sufficient accuracy at any measurement time, the speed may also be firmly prescribed as a parameter.

A digital signal processor which preferably also forms the second filter unit is preferably used to control the A/D converter stage, i.e., the selection of the trigger times, and to process the digital signal provided by the A/D converter stage. The drive device for triggering the A/D converter stage preferably has a source (which may be formed by a timer) for a binary signal and a divider which is used to divide the binary signal by an integer in order to generate the trigger signal for the A/D converter stage, the binary signal being processed by a curve shaper in order to provide the supply voltage for the transmitter. The timer may be part of the digital signal processor or may be separate therefrom. The divider is preferably separate from the signal processor and is in the form of a PAL (Programmable Array Logic) module.

The invention will be explained, by way of example, in more detail below with reference to the accompanying drawings.

BRIEF DESCRIPTION OF THE DRAWINGS

FIG. 2 schematically shows one example of the profile of a probe signal during digital sampling.

DETAILED DESCRIPTION OF THE INVENTION

Figure 1:
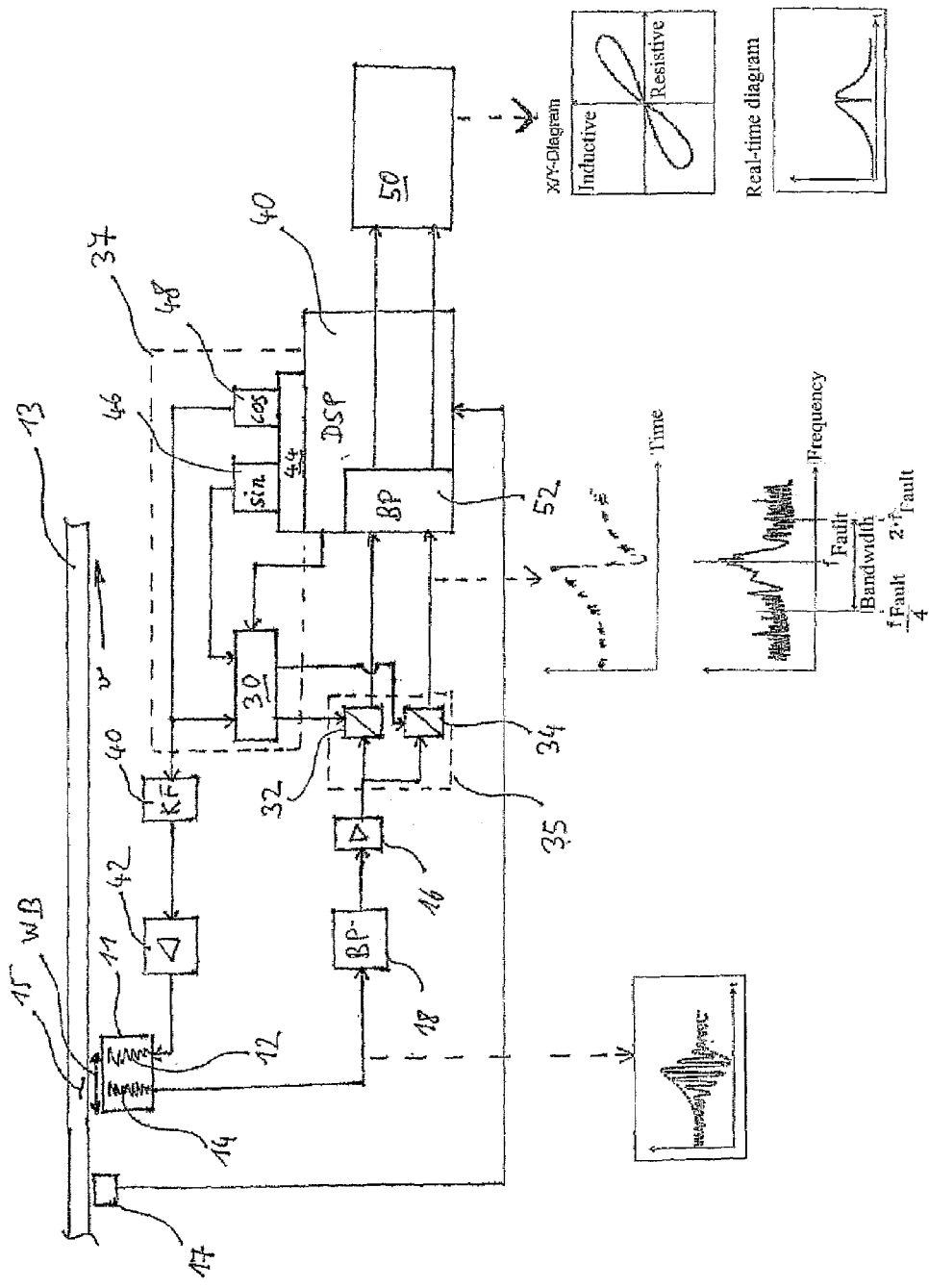
FIG. 1 schematically shows one example of an embodiment of an eddy current measuring apparatus according to the present invention.

FIG. 1 shows one example of the design of an eddy current measuring apparatus according to the invention. In this case, a test specimen 13, which is in the form of an industrial semifinished product, for example, a slab, is moved linearly past a test station 1 at a variable speed v is tested, the speed being detected by means of a speed sensor 17 which, for example, can emit a signal that is essentially proportional to the speed v. In this case, the signal may be, for example, a square-wave signal which, for example, contains one pulse for every 5 mm of forward feed of the test specimen 13.

The test station 11 has a transmitter in the form of a transmission coil 12 and a probe in the form of a reception coil 14. The transmission coil 12 is used to induce eddy currents in the test specimen 13 by means of an electromagnetic alternating field at least one prescribed carrier frequency the eddy currents, in turn, inducing an AC voltage in the reception coil 14 which acts as a probe signal and has a carrier oscillation at the carrier frequency of the transmission coil 12. The amplitude and the phase of the probe signal is modulated as a result of a fault 15 if the fault 15 reaches the effective width WB of the reception coil 14. The reception coil 14 is preferably in the form of a differential coil, that is say, in the form of a coil which has two windings (which are wound in opposite directions) and reacts only to changes in the electrical properties of the test specimen on account of the presence of a fault 15. Differential coils are suited, in particular, to detecting sudden changes in the test specimen 13. However, instead, an absolute coil could also be used as the reception coil 14, the absolute coil comprising a plurality of windings which are wound in the same direction and being suited, in particular, to detecting long homogeneous changes in the test specimen 13.

The voltage for the transmission coil 12 may be generated, for example, by a binary signal which is generated by a timer unit 44 being supplied as a predefined frequency to a generator 48 which uses that frequency to generate a square-wave signal or else a sinusoidal signal which passes through a curve shaper 40 and is then amplified by means of a power amplifier 42 before it is supplied to the transmission coil 12. The signal preferably has a sinusoidal waveform, and in the simplest case, contains only a single carrier frequency. However, measurements involving a plurality of carrier frequencies at the same time and/or carrier signals which differ considerably from sinusoidal oscillations are also possible, in principle. The carrier frequency is typically in the range from 1 kHz to 5 MHz.

The probe signal picked up by the reception coil 14 passes though a bandpass filter 18 and an adjustable preamplifier 16 before it is supplied to an A/D converter stage 35. The bandpass filter 18 is used, on the one hand, by means of the low-pass filter, as an anti-aliasing filter as regards the digitization of the signal by the A/D converter stage 35, and is used, on the other hand, by means of the high-pass filter, to remove low-frequency interference signals. The adjustable preamplifier 16 is used to change the amplitude of the analog probe signal to the amplitude which is optimally suited to the A/D converter stage 35, The A/D converter stage 35 has two A/D converters 32, 34 which are connected in parallel and should have a high resolution, but at least a resolution of 16 bits, preferably at least 22 bits, and should preferably be able to carry out at least 500 A/D conversions per second. The A/D converters 32, 34 are preferably in the form of flash converters or SAR (Successive Approximation Register) converters.

The A/D converter stage 35 is triggered by a drive device 37 which has the timer unit 44, the cosine generator 48, a sine generator 46 which is arranged parallel to the sine generator 46, and a frequency divider 30. The signal which is generated by the cosine generator 48 (which is at the frequency of the carrier frequency of the supply signal for the transmission coil 12) and the signal from the sine generator 46 (which corresponds to the signal from the cosine generator 48 but has been phase-shifted through 90° with respect to the signal from the cosine generator 48) are present at the input of the frequency divider 30. In the frequency divider 30, the frequency of these two signals is divided by an integer n.

The corresponding output signal whose frequency has been reduced is used to trigger the A/D converter 32 or the A/D converter 34. The number n for the divider 30 is selected by a digital signal processor 40 as a function of the fault frequency, i.e., the quotient of the instantaneous test specimen speed v and the effective width WB of the reception coil 14. The value of n is preferably selected to be inversely proportional to the fault frequency so that the trigger rate of the A/D converter stage 35 is at least approximately proportional to the fault frequency. In this manner, if the effective width WB is assumed to be constant to a first approximation and if the test specimen speed v is higher, and thus, the fault frequency is higher, the analog probe signal is correspondingly sampled more frequently.

The divider 30 is preferably in the form of a so-called PAL (Programmable Array Logic) module in order to ensure that the trigger signals arrive at the A/D converter stage 35 in a manner such that they have been delayed as little as possible (i.e., synchronously) with respect to the output signal from the cosine generator 48 and from the sine generator 46 and have no phase jitter.

On account of the corresponding phase shift between the two input signals for the divider 30, the two A/D converters 32, 34 are also triggered with a fixed phase offset of 90°. This makes it possible for the analog probe signal to be evaluated in two components, i.e., both in terms of amplitude and phase. It goes without saying that the phase delay between the trigger signal for the A/D converter stage 35 and the signal from the transmission coil 12 should be as short as possible, in which case so-called phase jitter, in particular, should also be avoided, i.e., the phase relationships should be as precisely constant as possible in terms of time.

The drive device 37 shown is used to ensure that the analog probe signal is sampled at most once per fill cycle of the carrier oscillation by each A/D converter 32, 34 (in this case, n is equal to 1). However, depending on the instantaneous fault frequency, that is to say the test specimen speed v, n may become considerably larger than 1, with the result that only one sampling operation is carried out at all during every nth full cycle of the carrier oscillation.

FIG. 2 shows an example in which n is equal to 2, i.e., each A/D converter 32, 34 carries out one respective sampling operation $A_n$, $B_n$ only during every second full cycle.

Since, however, in all cases, sampling is carried out at most once per full cycle for each A/D converter 32, 34, this undersampling results in the frequency of the carrier oscillation, i.e., the carrier frequency, being eliminated from the digital signal, i.e., undersampling is used to demodulate the analog probe signal.

The value of n is preferably selected in such a manner that at least 5, preferably at least 20, sampling operations are carried out by each A/D converter 32, 34 in the interval of time in which a significant fault signal is observed, that is to say in the interval of time which a point of the fault 15 moves through the effective width WB of the reception coil 14, that is to say in the interval of time which essentially corresponds to the inverse of the fault frequency, in order to obtain the information contained in the fault signal in a manner which still suffices for reliable fault detection. However, no more than 50, and at most 100, sampling operations will generally be necessary during such an interval of time.

The frequency of the carrier oscillation should be selected in such a manner that is at least ten times the fault frequency since the fault signal will otherwise be carried by too few full cycles of the carrier oscillation and the ability to reproduce the fault will become problematical. If, on account of other boundary conditions, the carrier frequency cannot be selected to be high enough, fault detection can be improved by synchronously sampling once in each first half-cycle and in each second half-cycle, the value from the second half-cycle being inverted and then being processed further like the value from the first half-cycle (on account of the inversion, this still constitutes undersampling as regards the carrier frequency).

The demodulated digital two-channel output signal from the A/D converter stage 35 passes through a digital bandpass filter 52 which can be represented by the signal processor 40 and is used to remove interference signals which are outside the bandwidth of the fault signal. For this purpose, the cut-off frequency of the high-pass filter is preferably selected in such a manner that it is less than one quarter of the fault frequency, while the cut-off frequency of the low-pass filter is preferably selected in such a manner that is at least twice the fault frequency in order to avoid removing signal components which still contain information regarding the fault.

The digital bandpass filter 52 is clocked at the sampling rate of the A/D converter stage 35, i.e., the trigger rate, which includes the great advantage that, when the fault frequency is changed, i.e., when the test specimen speed v is changed, the cut-off frequencies of the bandpass filter are automatically entrained with the fault frequency since the cut-off frequencies of a digital bandpass filter are proportional to the clock rate and the clock rate is automatically matched to the change in the fault frequency via the sampling rate which is prescribed by the drive unit 37.

The information regarding the effective width WB that is needed to determine the fault frequency can be either manually input to the signal processor 40 or it is directly provided by the test station 11, as is described, for example, in EP 0 734 522 B1 and corresponding International Patent Application PCT/EP94/03811 which designates the United States and was published as WO095/169125.

It goes without saying that the measuring system reacts analogously to a change in the fault frequency, said change being caused by the fact that, although the test specimen speed v is kept constant, the reception coil 14 is replaced with another reception coil having a different effective width WB.

The useful signal obtained after filtering by the digital bandpass filter 52 is evaluated in a manner known per se in an evaluation unit 50 in order to detect and locate faults 15 in the test specimen 13, both the amplitude and the phase information for the fault signal usually being used here.

In particular, given relatively large values of n, i.e., if only a relatively small number of full cycles of the carrier oscillation are sampled at all, the transmission coil 12 and/or the evaluation electronics, i.e., the signal processor 40, in particular, can, for example, be switched off or put into the quiescent state during the sampling pauses in order to reduce the power consumption, which is important, in particular, for portable measuring devices.

The invention claimed is:

1. A method for the nondestructive and contact-free detection of faults, in a test specimen which is moved relative to a probe having an effective width, comprising the steps of:
   using a transmitter to apply periodic electromagnetic alternating fields to the test specimen and using the probe to detect a periodic electrical signal which has a carrier oscillation of which at least one of its amplitude and phase is modulated as a result of a fault in the test specimen if the fault reaches the effective width of the probe,
   filtering a signal from the probe using a frequency-selective first filter unit,
   sampling the signal which has been filtered using the first filter unit by means of a triggerable A/D converter stage to obtain a demodulated digital measurement signal,
   filtering the digital measurement signal using a digital frequency-selective adjustable second filter unit to obtain a useful signal, and
   evaluating the useful signal to detect a fault in the test specimen,
   wherein said sampling by the A/D converter stage is triggered at an nth integer fraction of the frequency of the carrier oscillation, n being selected as a function of the fault frequency which is obtained as the quotient of the relative speed between the test specimen and the probe and the effective width of the probe, and wherein the frequency-selective adjustable second filter unit is adjusted as a function of the fault frequency.

2. The method as claimed in claim 1, wherein the test specimen is moved linearly with respect to the probe for producing the relative movement between the test specimen and the probe.

3. The method as claimed in claim 1, wherein the probe is rotated for producing the relative movement between the test specimen and the probe.

4. The method as claimed in claim 1, wherein the transmitter is a coil to which a radio frequency AC voltage in the frequency range from 1 kHz to 5 MHz is applied to induce eddy currents in the test specimen, and wherein the probe is a coil arrangement in which the eddy currents induce the periodic signal.

5. The method as claimed in claim 1, wherein the transmitter is supplied with an AC voltage for generating the periodic electromagnetic alternating fields, the AC voltage being generated from a binary signal by curve shaping.

6. The method as claimed in claim 5, wherein the trigger signal for the A/D converter stage is generated by dividing the frequency of the binary signal that is used to generate the AC voltage for the transmitter by n.

7. The method as claimed in claim 1, wherein n is selected to be inversely proportional to the fault frequency for causing a trigger rate of the A/D converter stage to be at least approximately proportional to the fault frequency.

8. The method as claimed in claim 1, wherein n is selected in such a manner that at least 5 sampling operations are carried out by the A/D converter stage in an interval of time which corresponds to the inverse of the fault frequency.

9. The method as claimed in claim 1, wherein n is selected in such a manner that at most 100 sampling operations are carried out by the A/D converter stage in an interval of time which corresponds to the inverse of the fault frequency.

10. The method as claimed in claim 1, wherein the frequency-selective adjustable second filter unit is automatically adjusted as a function of the fault frequency by the second filter unit being clocked at the sampling rate of the A/D converter stage.

11. The method as claimed in claim 1, wherein the second filter unit has a low-pass filter which removes interference components of the demodulated digital signal at frequencies higher than the fault frequency, the low-pass filter having a cut-off frequency of set higher than the fault frequency.

12. The method as claimed claim 1, wherein the second filter unit has a high-pass filter which removes DC components of the demodulated digital signal, the high-pass filter having a cut-off frequency set lower than the fault frequency.

13. The method as claimed in claim 1, wherein the frequency of the carrier oscillation is selected to be at least ten times the fault frequency.

14. The method as claimed in claim 1, wherein the A/D converter stage, when it is triggered, samples two values in a manner offset by a fixed phase difference for obtaining the digital measurement signal in the form of a two-component signal.

15. The method as claimed in claim 14, wherein the phase difference is m*360°+90°, where m is zero or an integer.

16. The method as claimed in claim 14, wherein the two components of the digital measurement signal provided by the A/D converter stage are filtered separately using the second filter unit for obtaining the useful signal in the form of a two-component signal.

17. The method as claimed in claim 16, wherein the two components of the useful signal are taken into account when evaluating the useful signal.

18. The method as claimed in claim 1, comprising the further step of interrupting the application of the electromagnetic alternating field to the test specimen using the transmitter for at least part of each interval between two successive trigger signals for the A/D converter stage.

19. The method as claimed in claim 1, wherein the first filter unit has at least one low-pass filter which is used as an aliasing filter for the sampling by the A/D converter stage.

20. The method as claimed in claim 1, wherein the first filter unit has a high-pass filter which is used to remove low-frequency interference signals.

21. The method as claimed in claim 1, further comprising the step of determining the relative speed between the test specimen and the probe.

22. The method as claimed in claim 1, wherein a predetermined value is used as the relative speed between the test specimen and the probe.

23. The method as claimed in claim 1, wherein a controllable amplifier is connected upstream of the A/D converter stage and is used for changing the signal to an amplitude which is optimally suited to the A/D converter stage.

24. The method as claimed in claim 1, wherein the transmitter uses electromagnetic excitation to deliver sound waves to the test specimen, and wherein the probe detects sound waves in the test specimen and converts the sound waves into said periodic electrical signal.

25. The method as claimed in claim 1, wherein the transmitter radiates microwaves into the test specimen, and the probe converts the microwaves into said periodic electrical signal.

26. The apparatus as claimed in claim 1, wherein the A/D converter stage has a resolution of at least 16 bits.

27. The apparatus as claimed in claim 1, wherein the A/D converter stage has at least one flash converter or SAR converter.

28. The apparatus as claimed in claim 1, wherein the second filter unit comprises a digital signal processor.

29. The apparatus as claimed in claim 1, wherein the A/D converter stage comprises two A/D converters which are connected in parallel, the two A/D converters being triggered at the same frequency and sample in a manner offset by a fixed phase difference to obtain the digital measurement signal in the form of a two-component signal.

30. An apparatus for the nondestructive and contact-free detection of faults in a test specimen, said apparatus comprising:
- a device for detecting the relative speed between the test specimen and the probe,
- a transmitter for applying periodic electromagnetic alternating fields to the test specimen,
- a probe having an effective width for detecting a periodic electrical signal which has a carrier oscillation with one of an amplitude and a phase that is modulated as a result of a fault in the test specimen if the fault reaches the effective width of the probe,
- a frequency-selective first filter unit for filtering a signal from the probe,
- a triggerable A/D converter stage for sampling the signal which has been filtered using the first filter unit to obtain a demodulated digital measurement signal,
- a drive device for triggering the A/D converter stage at an nth integer fraction of the frequency of the carrier oscillation, n being a function of a fault frequency which is obtained as the quotient of the relative speed between the test specimen and the probe and the effective width of the probe,
- a digital frequency-selective second filter unit which is adjustable as a function of the fault frequency and which filters the digital measurement signal for obtaining a useful signal, and
- an evaluation unit for evaluating the useful signal for the purpose of detecting a fault in the test specimen.

31. The apparatus as claimed in claim 30, the probe is one of a differential coil and an absolute coil for measuring eddy currents.

32. The apparatus as claimed in claim 30, wherein a binary signal source and a curve shaper are provided for generating a supply voltage signal for the transmitter from a binary signal by means of curve shaping.

33. The apparatus as claimed in claim 32, wherein the drive device has a divider for generating the trigger signal for the A/D converter stage from the binary signal for the curve shaper by dividing said binary signal by n.

34. The apparatus as claimed in claim 33, characterized in that the binary signal source is in the form of a timer (44).

* * * * *